(12) United States Patent
Deur-Bert et al.

(10) Patent No.: US 10,633,309 B2
(45) Date of Patent: *Apr. 28, 2020

(54) METHOD FOR PRODUCING TETRAFLUOROPROPENE

(71) Applicant: Arkema France, Colombes (FR)

(72) Inventors: Dominique Deur-Bert, Charly (FR);
Dominique Garrait, Charly (FR);
Anne Pigamo, Francheville (FR);
Laurent Wendlinger, Soucieu en Jarrest (FR)

(73) Assignee: ARKEMA FRANCE, Colombes (FR)

(*) Notice: Subject to any disclaimer, the term of this patent is extended or adjusted under 35 U.S.C. 154(b) by 0 days.

This patent is subject to a terminal disclaimer.

(21) Appl. No.: 16/099,235

(22) PCT Filed: May 17, 2017

(86) PCT No.: PCT/FR2017/051186
§ 371 (c)(1),
(2) Date: Nov. 6, 2018

(87) PCT Pub. No.: WO2017/198946
PCT Pub. Date: Nov. 23, 2017

(65) Prior Publication Data
US 2019/0218162 A1     Jul. 18, 2019

(30) Foreign Application Priority Data
May 19, 2016 (FR) ........................ 1654444

(51) Int. Cl.
C07C 17/20 (2006.01)
B01J 8/02 (2006.01)
(Continued)

(52) U.S. Cl.
CPC ............ *C07C 17/206* (2013.01); *B01J 8/025* (2013.01); *B01J 8/0278* (2013.01);
(Continued)

(58) Field of Classification Search
CPC ..... C07C 17/013; C07C 17/206; C07C 21/18; B01J 8/025; B01J 8/0278; B01J 19/2445; B01J 2219/00038; Y02P 20/584
See application file for complete search history.

(56) References Cited

U.S. PATENT DOCUMENTS

2014/0012051 A1 * 1/2014 Pigamo .................. B01J 37/14
570/160

FOREIGN PATENT DOCUMENTS

WO   2007/079431 A2   7/2007
WO   2008/040969 A2   4/2008
(Continued)

OTHER PUBLICATIONS

ISA/EP; International Search Report and Written Opinion for International Application No. PCT/FR2017/051186 dated Sep. 13, 2017.

*Primary Examiner* — Jafar F Parsa
(74) *Attorney, Agent, or Firm* — NK Patent Law

(57) ABSTRACT

The present invention concerns a method for preparing tetrafluoropropene utilising three reactors each comprising a catalytic bed containing a catalyst or a preliminary catalyst, and comprising the implementation, separately in each of the reactors, of catalytic reactions or reactions regenerating the catalyst, the quantity of catalyst or preliminary catalyst in the catalytic bed of one of the reactors representing between 90% and 110% of the quantity of catalyst or preliminary catalyst contained in the catalytic bed of one of the other two reactors. The present invention also concerns a facility configured to implement the present method.

10 Claims, 4 Drawing Sheets

(51) Int. Cl.
  *B01J 19/24* (2006.01)
  *C07C 17/013* (2006.01)
(52) U.S. Cl.
  CPC ......... *B01J 19/2445* (2013.01); *C07C 17/013* (2013.01); *B01J 2219/00038* (2013.01); *Y02P 20/584* (2015.11)

(56) References Cited

FOREIGN PATENT DOCUMENTS

| | | |
|---|---|---|
| WO | 2008/054781 A1 | 5/2008 |
| WO | 2009/118628 A1 | 10/2009 |
| WO | 2012/098421 A1 | 7/2012 |
| WO | 2012/098422 A1 | 7/2012 |
| WO | 2013/088195 A1 | 6/2013 |
| WO | 2013/182816 A1 | 12/2013 |
| WO | 2014/025065 A1 | 2/2014 |
| WO | 2016/001515 A1 | 1/2016 |

* cited by examiner

METHOD FOR PRODUCING TETRAFLUOROPROPENE

CROSS-REFERENCE TO RELATED APPLICATIONS

This application is a National Stage application of International Application No. PCT/FR2017/051186, filed on May 17, 2017, which claims the benefit of French Patent Application No. 1654444, filed on May 19, 2016, the entire contents of which are all hereby incorporated herein by reference.

FIELD OF THE INVENTION

The present invention relates to a process for the manufacture of tetrafluoropropene (HFO-1234) and in particular of 2,3,3,3-tetrafluoropropene (HFO-1234yf), and to a plant suitable for the implementation of this process.

TECHNOLOGICAL BACKGROUND

Greenhouse gases are gaseous components which absorb the infrared radiation emitted by the surface of the Earth, thus contributing to the greenhouse effect. The increase in their concentration in the atmosphere is one of the factors causing global warming.

The production of the chlorofluorocarbons (CFCs) and hydrochlorofluorocarbons (HCFCs) used in refrigeration and air conditioning systems has thus been successively regulated by the Montreal protocol and then the Kyoto protocol. There exists a need to develop new molecules which are just as effective and which in particular exhibit the smallest possible global warming potential. This is the case with hydrofluoroolefins and in particular HFO-1234yf, which is a particularly useful compound.

It is known to produce hydrofluoroolefins or hydrofluorocarbons by fluorination of hydrochloroolefins or of hydrochlorocarbons in particular. This fluorination is generally a catalytic fluorination using hydrofluoric acid as fluorinating agent.

The fluorination reaction generally has to be carried out at a high temperature (more than 300° C.) in the gas phase, in the presence of a supported or bulk solid catalyst.

It is known to provide cofeeding with an oxidizing agent, in particular air, or optionally chlorine, in order to preserve the lifetime of the catalyst and to limit the deposition of coke at its surface during the reaction stage.

The document U.S. Pat. No. 8,614,361 describes a process for the manufacture of HFO-1234yf by reacting HCFO-1233xf with HF in the presence of a high oxygen content.

The document U.S. Pat. No. 8,618,338 describes a process for the manufacture of fluoroolefin in two stages, in particular a first stage of reaction in the liquid phase starting from 1,1,2,3-tetrachloropropene (HCO-1230xa), in order to obtain the intermediate HCFO-1233xf, and a second stage of reaction in the gas phase starting from HCFO-1233xf, in order to obtain HFO-1234yf.

The document WO 2013/088195 teaches a process for the manufacture of HFO-1234yf in two stages, a first stage of fluorination in the gas phase of 1,1,1,2,3-pentachloropropane (HCC-240db) and/or of 1,1,2,2,3-pentachloropropane (HCC-240aa), in order to obtain the intermediate HCFO-1233xf, and then a second stage of reaction in the gas phase starting from HCFO-1233xf, in order to obtain HFO-1234yf.

The documents WO 2012/098421 and WO 2012/098422 teach the activation and the regeneration of fluorination catalysts.

The document WO 2013/182816 describes a chemical reaction process for the alternating implementation of a phase of catalytic reaction and of a phase of regeneration of catalyst in a reactor.

The document WO2016/001515 describes a chemical reaction process for the alternating implementation of a phase of catalytic reaction and of a phase of regeneration of catalyst in one or more reactors.

There still exists a need to improve the processes for the manufacture of HFO-1234 compounds, such as HFO-1234yf, and in particular to produce these compounds with a high yield and with a high degree of purity while minimizing the production costs and the capital costs.

SUMMARY OF THE INVENTION

According to a first aspect, the present invention relates to a process for the manufacture of tetrafluoropropene employing three reactors each comprising a catalytic bed containing a catalyst or a preliminary catalyst and comprising the implementation, independently in each of the reactors, of:
  at least one stage of reaction in the gas phase of a compound A in the presence of hydrofluoric acid and of a preliminary catalyst, in order to form a compound B;
  at least one stage of reaction in the gas phase of a compound B in the presence of hydrofluoric acid and of a catalyst, in order to form the tetrafluoropropene, or
  a stage of regeneration of the catalyst or of the preliminary catalyst by bringing the latter into contact with a regeneration stream comprising an oxidizing agent,
  characterized in that the amount of catalyst or of preliminary catalyst in the catalytic bed of one of the reactors represents between 90% and 110% of the amount of catalyst or of preliminary catalyst present in the catalytic bed of one of the other two reactors.

Preferably, the amount of catalyst or of preliminary catalyst present in the catalytic bed of each reactor is between 90% and 110% of the amount of catalyst or of preliminary catalyst present in the catalytic bed of the other two reactors considered independently of one another, advantageously between 92% and 108%, preferably between 95% and 105%, in particular between 98% and 102%.

According to a preferred embodiment, the amount of catalyst or of preliminary catalyst present in the catalytic bed of each reactor is identical in the three reactors.

According to a preferred embodiment, the stage of reaction of a compound B in the presence of hydrofluoric acid or the stage of reaction of a compound A in the presence of hydrofluoric acid is carried out alternately with a stage of regeneration of the catalyst or of the preliminary catalyst.

According to a preferred embodiment, the present process simultaneously employs:
  a stage of reaction of a compound A in the presence of hydrofluoric acid in one of the three reactors;
  a stage of reaction of a compound B in the presence of hydrofluoric acid in another of the three reactors;
  a stage of regeneration of the catalyst or of the preliminary catalyst or a waiting stage in the third reactor.

According to a preferred embodiment, the process comprises:
  the collecting of a stream of products on conclusion of the stage of reaction of the compound B;
  the use of said stream of products collected on conclusion of the stage of reaction of the compound B in order to carry out the stage of reaction of the compound A in the presence of hydrofluoric acid; and the separation of the stream of products resulting from the stage of reaction of the compound A in the presence of hydrofluoric acid into a first stream comprising hydrochloric acid and tetrafluoropropene and a second stream comprising hydrofluoric acid and the compound B;

optionally, the collecting of said second stream comprising hydrofluoric acid and the compound B, and the recycling of this in the stage of reaction of the compound B in the presence of hydrofluoric acid or in the stage of reaction of a compound A in the presence of hydrofluoric acid.

According to a preferred embodiment, the tetrafluoropropene is 2,3,3,3-tetrafluoropropene (HFO-1234yf) or 1,3,3,3-tetrafluoropropene (HFO-1234ze).

According to a preferred embodiment, the compound A is chosen from tetrachloropropenes, chlorotrifluoropropenes, pentachloropropanes, dichlorotrifluoropropanes, trichlorodifluoropropanes, tetrachlorofluoropropanes, dichlorodifluoropropenes, trichlorofluoropropenes and the mixtures of these; the compound B is chosen from chlorotrifluoropropenes, pentafluoropropanes, dichlorotrifluoropropanes, trichlorodifluoropropanes, tetrachlorofluoropropanes, dichlorodifluoropropenes, trichlorofluoropropenes and the mixtures of these; preferably, the compound A is selected from the group consisting of 2-chloro-3,3,3-trifluoro-1-propene (HCFO-1233xf), 2,3-dichloro-1,1,1-trifluoropropane (HCFC-243db), 1,1,1,2,3-pentachloropropane (HCC-240db), 1,1,2,2,3-pentachloropropane (HCC-240aa), 1,1,1,3,3-pentachloropropane (HCC-240fa), 1,1,2,3-tetrachloro-1-propene (HCO-1230xa), 2,3,3,3-tetrachloro-1-propene (HCO-1230xf), 1,1,3,3-tetrachloro-1-propene (HCO-1230za) and 1,3,3,3-tetrachloro-1-propene (HCO-1230zd); and the compound B is selected from the group consisting of 2-chloro-3,3,3-trifluoro-1-propene (HCFO-1233xf), 1,1,1,2,2-pentafluoropropane (HFC-245cb) and 1-chloro-3,3,3-trifluoro-1-propene (HCFO-1233zd).

According to a second aspect, the present invention provides a plant for the manufacture of tetrafluoropropene comprising three reactors for reaction in the gas phase each comprising a catalytic bed containing a catalyst or a preliminary catalyst, the three reactors for reaction in the gas phase each being configured in order to be fed by:

a device for feeding with reaction stream comprising a compound B and hydrofluoric acid; and/or a device for feeding with preliminary reaction stream comprising a chlorinated compound A and hydrofluoric acid; and/or a device for feeding with regeneration stream configured in order to feed the reactor with a regeneration stream comprising an oxidizing agent; and optionally, a device for feeding with waiting stream configured in order to feed a reactor with a gaseous stream comprising an inert gas;

characterized in that the amount of catalyst or of preliminary catalyst in the catalytic bed of one of the reactors is from 90% to 110% of the amount of catalyst or of preliminary catalyst present in the catalytic bed of one of the other two reactors.

According to a preferred embodiment, the amount of catalyst or of preliminary catalyst present in the catalytic bed of each reactor is between 90% and 110% of the amount of catalyst or of preliminary catalyst present in the catalytic bed of the other two reactors considered independently of one another, advantageously between 92% and 108%, preferably between 95% and 105%, in particular between 98% and 102%.

According to a preferred embodiment, the amount of catalyst or of preliminary catalyst present in the catalytic bed of each reactor is identical in the three reactors.

According to a preferred embodiment, the tetrafluoropropene is 2,3,3,3-tetrafluoropropene or 1,3,3,3-tetrafluoropropene.

According to a preferred embodiment, the plant comprises:
a first reactor, a second reactor and a third reactor;
a first device for collecting stream of products resulting from the first reactor connected at the outlet of the latter;
a second device for collecting stream of products resulting from the second reactor connected at the outlet of the latter;
a third device for collecting stream of products resulting from the third reactor connected at the outlet of the latter;
a first intermediate collecting device connected to any one of the devices for collecting stream of products resulting from the first, from the second and/or from the third reactor and joined to the device for feeding with preliminary reaction stream;
a second intermediate collecting device connected to any one of the devices for collecting stream of products resulting from the first, from the second and/or from the third reactor and joined to the separation unit;
a separation unit fed by the second intermediate collecting device;
a first collecting pipe and a second collecting pipe which are connected at the outlet of the separation unit, the first collecting pipe being configured in order to transport a stream comprising hydrochloric acid and tetrafluoropropene and the second collecting pipe being configured in order to transport a stream comprising hydrofluoric acid and compound B;
a device for feeding with reaction stream configured in order to feed the first reactor, the second reactor and the third reactor, this device being itself fed by a device for feeding with hydrofluoric acid and optionally by the second collecting pipe;
a device for feeding with preliminary reaction stream configured in order to feed the first reactor, the second reactor and the third reactor, this device being itself fed by a device for feeding with hydrofluoric acid and optionally by the first intermediate collecting device;
a device for feeding with regeneration stream configured in order to feed the first reactor, the second reactor and the third reactor;
a device for collecting stream of gas resulting from the regeneration of the first reactor, of the second reactor and of the third reactor.

According to another preferred embodiment, the plant comprises:
a first reactor, a second reactor and a third reactor;
a first device for collecting stream of products resulting from the first reactor connected at the outlet of the latter;
a second device for collecting stream of products resulting from the second reactor connected at the outlet of the latter;
a third device for collecting stream of products resulting from the third reactor connected at the outlet of the latter;

a third intermediate collecting device connected to any one of the devices for collecting stream of products and joined to the device for feeding with reaction stream;

a second intermediate collecting device connected to any one of the devices for collecting stream of products resulting from the first, from the second and/or from the third reactor and joined to the separation unit;

a separation unit fed by the second intermediate collecting device;

a first collecting pipe and a second collecting pipe which are connected at the outlet of the separation unit, the first collecting pipe being configured in order to transport a stream comprising hydrochloric acid and tetrafluoropropene and the second collecting pipe being configured in order to transport a stream comprising hydrofluoric acid and compound B;

a device for feeding with reaction stream configured in order to feed the first reactor, the second reactor and the third reactor, this device being itself fed by a device for feeding with hydrofluoric acid, and by the third intermediate collecting device and optionally by the second collecting pipe;

a device for feeding with preliminary reaction stream configured in order to feed the first reactor, the second reactor and the third reactor, this device being itself fed by a device for feeding with hydrofluoric acid and optionally by the second collecting pipe;

a device for feeding with regeneration stream configured in order to feed the first reactor, the second reactor and the third reactor;

a device for collecting stream of gas resulting from the regeneration of the first reactor, of the second reactor and of the third reactor.

According to a preferred embodiment, the reactors are made of steel and have an interior surface covered with an alloy comprising more than 30% by weight of nickel or with a coating of fluoropolymers type; preferably, the alloy comprising more than 30% by weight of nickel is an Incolloy®, Inconel®, Monel® or Hastelloy®.

DETAILED DESCRIPTION OF THE INVENTION

Figure 1A:
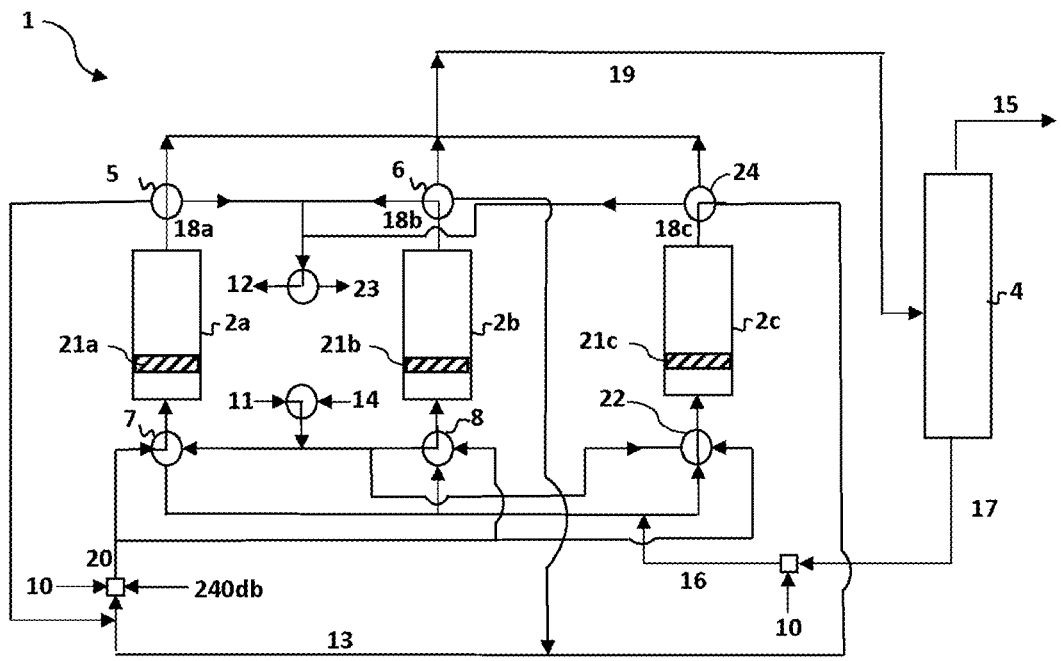
FIGS. 1a and 1b diagrammatically represent an embodiment of a plant according to the invention with three reactors in different operating configurations.

The invention is now described in greater detail and in a nonlimiting manner in the description which follows. Unless otherwise mentioned, the percentages and proportions shown are values by weight. The invention provides for the production of HFO-1234 by catalytic reaction in the gas phase; this catalytic reaction is, according to the invention, alternated with the regeneration of the catalyst. In some embodiments, the invention provides for the production of HFO-1234 in several stages.

According to a first aspect of the present invention, a process for the manufacture of tetrafluoropropene is provided. Said process for the manufacture of tetrafluoropropene employs three reactors each comprising a catalytic bed containing a catalyst or a preliminary catalyst and comprises the implementation, independently in each of the reactors, of:

at least one stage of reaction in the gas phase of a compound A in the presence of hydrofluoric acid and of a preliminary catalyst, in order to form a compound B;

at least one stage of reaction in the gas phase of a compound B in the presence of hydrofluoric acid and of a catalyst, in order to form the tetrafluoropropene, or a stage of regeneration of the catalyst or of the preliminary catalyst by bringing the latter into contact with a regeneration stream comprising an oxidizing agent.

Preferably, the amount of catalyst or of preliminary catalyst in the catalytic bed of one of the reactors is from 90% to 110% of the amount of catalyst or of preliminary catalyst present in the catalytic bed of one of the other two reactors.

According to a preferred embodiment, the amount of catalyst or of preliminary catalyst present in the catalytic bed of each reactor is between 90% and 110% of the amount of catalyst or of preliminary catalyst present in the catalytic bed of the other two reactors considered independently of one another, advantageously between 92% and 108%, preferably between 95% and 105%, in particular between 98% and 102%.

According to a specific embodiment, the amount of catalyst or of preliminary catalyst present in the catalytic bed of each reactor is identical in the three reactors. Preferably, the catalyst is the same catalyst as the preliminary catalyst.

Said catalyst or said preliminary catalyst used in the present process can, for example, be based on a metal comprising a transition metal oxide or a derivative or a halide or an oxyhalide of such a metal. Mention may be made, for example, of $FeCl_3$, chromium oxyfluoride, chromium oxides (optionally subjected to fluorination treatments), chromium fluorides and their mixtures. Other possible catalysts are catalysts supported on carbon, antimony-based catalysts or aluminum-based catalysts (for example $AlF_3$ and $Al_2O_3$, aluminum oxyfluoride and aluminum fluoride).

Use may be made in general of a chromium oxyfluoride, an aluminum fluoride or oxyfluoride, or a supported or nonsupported catalyst containing a metal such as Cr, Ni, Fe, Zn, Ti, V, Zr, Mo, Ge, Sn, Pb, Mg or Sb.

Reference may be made, in this regard, to the document WO 2007/079431 (on p. 7, I. 1-5 and 28-32), to the document EP 939 071 (section [0022]), to the document WO 2008/054781 (on p. 9, I. 22-p. 10, I. 34) and to the document WO 2008/040969 (claim 1), to which documents reference is expressly made.

The catalyst is more particularly preferably chromium-based and it is more particularly a mixed catalyst comprising chromium.

According to one embodiment, use is made, for any one of the reaction stages, of a mixed catalyst comprising chromium and nickel. The Cr/Ni molar ratio (on the basis of the metal element) is generally from 0.5 to 5, for example from 0.7 to 2, for example approximately 1. The catalyst can contain from 0.5% to 20% by weight of nickel.

The metal can be present in metallic form or in the form of a derivative, for example an oxide, halide or oxyhalide. These derivatives are preferably obtained by activation of the catalytic metal.

The support preferably consists of aluminum, for example alumina, activated alumina or aluminum derivatives, such as aluminum halides and aluminum oxyhalides, for example described in the document U.S. Pat. No. 4,902,838, or obtained by the activation process described above.

The catalyst can comprise chromium and nickel in an activated or nonactivated form, on a support which has or has not been subjected to an activation.

Reference may be made to the document WO 2009/118628 (in particular on p. 4, I. 30-p. 7, I. 16), to which reference is expressly made here.

Another preferred embodiment is based on a mixed catalyst or mixed preliminary catalyst containing chromium and at least one cocatalyst chosen from Co, Mn, Mg and Zn salts, preferably Zn salts. Said cocatalyst is preferably present in a content of 1% to 10% by weight, based on the weight of the catalyst.

The catalyst and the preliminary catalyst can be identical.

Before its use, the catalyst or the preliminary catalyst is preferably subjected to an activation with air, oxygen or chlorine and/or with HF. For example, the catalyst is preferably subjected to an activation with air or oxygen and HF at a temperature of 100 to 500° C., preferably of 250 to 500° C. and more particularly of 300 to 400° C. The duration of activation is preferably from 1 to 200 h and more particularly from 1 to 50 h. This activation can be followed by a final fluorination activation stage in the presence of an oxidizing agent, HF and organic compounds. The HF/organic compounds molar ratio is preferably from 2 to 40 and the oxidizing agent/organic compounds molar ratio is preferably from 0.04 to 25. The temperature of the final activation is preferably from 300 to 400° C. and its duration is preferably from 6 to 100 h.

According to one embodiment, the stage of reaction of a compound B in the presence of hydrofluoric acid or the stage of reaction of a compound A in the presence of hydrofluoric acid is carried out alternately with a stage of regeneration of the catalyst or of the preliminary catalyst.

The reaction in the gas phase in the presence of hydrofluoric acid of the compound B or of the compound A can be carried out:
- with an HF/compound B or compound A molar ratio of 3:1 to 150:1, preferably of 4:1 to 125:1 and more particularly preferably of 5:1 to 100:1;
- with a contact time of 3 to 100 s, preferably 4 to 75 s and more particularly 5 to 50 s (volume of catalyst divided by the total entering stream, adjusted to the operating temperature and pressure);
- at a pressure ranging from atmospheric pressure to 20 bar, preferably from 2 to 18 bar and more particularly from 3 to 15 bar;
- at a temperature (temperature of the catalytic bed) of 200 to 450° C., preferably of 250 to 400° C. and more particularly of 280 to 380° C.

The duration of the reaction stage is typically from 10 to 8000 hours, preferably from 50 to 5000 hours and more particularly preferably from 70 to 1000 hours.

An oxidizing agent, preferably oxygen, can optionally be added during the reaction. The oxygen/organic compounds molar ratio can be from 0.005 to 2, preferably from 0.01 to 1.5. Oxygen can be introduced in the pure form or in the form of air or of an oxygen/nitrogen mixture. Oxygen can also be replaced with chlorine.

Alternatively, the stage of reaction of the compound B or of the compound A in the presence of hydrofluoric acid is essentially carried out in the absence of oxygen and preferably essentially in the absence of any oxidizing agent.

According to one embodiment, the stage of regeneration of the catalyst or of the preliminary catalyst is carried out alternately with the stage of reaction of a compound B in the presence of hydrofluoric acid or with the stage of reaction of a compound A in the presence of hydrofluoric acid.

In each reactor used for carrying out the reaction of the compound B or of the compound A in the presence of HF, said reaction can be alternated with phases of regeneration of the catalyst. It is possible, for example, to pass from the reaction phase to the regeneration phase when the conversion of the compound B falls below a predetermined threshold, for example of 50%. If need be, beforehand, a transition period consisting in decompressing the reaction gas phase is provided. It can be followed by a phase of flushing using an inert gas or else of placing under vacuum with the aim of completely removing the reactants present.

According to a preferred embodiment, the regeneration of the catalyst or of the preliminary catalyst of the present process can comprise the treatment of said catalyst with a gaseous stream containing an oxidant.

According to one embodiment, the oxidant used is oxygen or air or an oxygen/nitrogen mixture or chlorine or a chlorine/nitrogen mixture. When the regeneration stage is carried out with air or an oxygen/nitrogen mixture, the proportion of oxygen can be from 5 mol % to approximately 100 mol %, with respect to the mixture of oxygen plus nitrogen.

According to another embodiment, the regeneration stage can be carried out with oxygen or air or an oxygen/nitrogen mixture or chlorine and HF. Advantageously, the regeneration stream contains at least 1 mol % of oxygen, with respect to the total regeneration stream. The proportion of oxygen can be from approximately 2 mol % to approximately 98 mol %, with respect to the mixture of oxygen plus HF, and from approximately 20 mol % to approximately 100 mol %, with respect to the mixture of oxygen plus nitrogen.

The temperature during the regeneration stage can range from 250 to 500° C., preferably from 300 to 450° C., more preferably from 350 to 400° C.

The regeneration stage can be carried out with a contact time of 1 to 200 s, preferably of 1 to 150 s, more preferably of 5 to 100 s; and for a time of 1 to approximately 1500 hours, preferably of 2 to 1000 hours, more preferably of 4 to 500 hours, particularly preferably of 10 to 200 hours, in particular of 15 to 150 hours.

The regeneration stage can be carried out at a pressure ranging from atmospheric pressure up to 20 bar.

According to a preferred embodiment, the temperature during the regeneration stage can be from approximately 250 to 500° C., with a contact time of from approximately 1 to 200 s, for a time of 10 to 200 hours and at a pressure ranging from atmospheric pressure to 20 bar.

The regeneration stage makes it possible to recover the initial activity of the catalyst. Several cycles can thus be linked together without to a significant extent detrimentally affecting the activity of the catalyst, which makes it possible to increase its lifetime.

On conclusion of the regeneration stage, the reactor can be placed under vacuum, so as to remove the inert gases and the oxygen which were introduced, prior to the reintroduction of the organic materials in the presence of hydrofluoric acid.

According to a preferred embodiment, the stage of reaction of a compound B in the presence of hydrofluoric acid is carried out in one of the three reactors while the stage of reaction of a compound A in the presence of hydrofluoric acid is carried out in one of the other two reactors.

According to a preferred embodiment, a regeneration stage is carried out in one of the three reactors while a stage of reaction of a compound B in the presence of hydrofluoric acid is carried out in one of the other two reactors. Preferably, a regeneration stage is carried out in one of the three reactors while a stage of reaction of a compound A in the presence of hydrofluoric acid is carried out in one of the other two reactors.

According to a preferred embodiment, said process also comprises the implementation of a waiting stage during which an inert gaseous stream feeds one of the three reactors; preferably, the inert gaseous stream consists of a stream of nitrogen, of argon, of helium or of a mixture of these. The waiting stage is preferably carried out before or after the regeneration stage.

According to a specific embodiment, the process according to the invention employs:
  a stage of reaction of a compound A in the presence of hydrofluoric acid in one of the three reactors;
  a stage of reaction of a compound B in the presence of hydrofluoric acid in another of the three reactors;
  a stage of regeneration of the catalyst or of the preliminary catalyst or a waiting stage in the third reactor.

According to a favored embodiment, the process according to the invention simultaneously employs:
  a stage of reaction of a compound B in the presence of hydrofluoric acid in one of the three reactors;
  a stage of reaction of a compound A in the presence of hydrofluoric acid in another of the three reactors;
  a stage of regeneration of the catalyst or of the preliminary catalyst or a waiting stage in the third reactor.

Preferably, the process comprises:
  the collecting of a stream of products on conclusion of the stage of reaction of the compound B;
  the use of said stream of products collected on conclusion of the stage of reaction of the compound B in order to carry out the stage of reaction of the compound A in the presence of hydrofluoric acid; and
  the separation of the stream of products resulting from the stage of reaction of the compound A in the presence of hydrofluoric acid into a first stream comprising hydrochloric acid and tetrafluoropropene and a second stream comprising hydrofluoric acid and the compound B;
  optionally, the collecting of said second stream comprising hydrofluoric acid and the compound B, and the recycling of this in the stage of reaction of the compound B in the presence of hydrofluoric acid or of the stage of reaction of the compound A.

Alternatively, the process comprises:
  the collecting of a stream of products on conclusion of the stage of reaction of the compound A;
  the use of said stream of products collected on conclusion of the stage of reaction of the compound A in order to carry out the stage of reaction of the compound B in the presence of hydrofluoric acid; and
  the separation of the stream of products resulting from the stage of reaction of the compound B in the presence of hydrofluoric acid into a first stream comprising hydrochloric acid and tetrafluoropropene and a second stream comprising hydrofluoric acid and the compound B;
  optionally, the collecting of said second stream comprising hydrofluoric acid and the compound B, and the recycling of this in the stage of reaction of the compound B in the presence of hydrofluoric acid or of the stage of reaction of the compound A.

According to a preferred embodiment, the reactors used in the present process are made of steel and have an interior surface covered with an alloy comprising more than 30% by weight of nickel or with a coating of fluoropolymers type; preferably, the alloy comprising more than 30% by weight of nickel is an Incolloy®, Inconel®, Monel® or Hastelloy®.

According to a specific embodiment, the tetrafluoropropene is 2,3,3,3-tetrafluoropropene or 1,3,3,3-tetrafluoropropene.

"Compound B" is understood to mean an organic compound comprising one or more carbon atoms. This compound preferably comprises 3 carbon atoms. This compound B is preferably a propane or a propene having one or more substituents chosen from F, Cl, I and Br (preferably from F and Cl). Preferably, the compound B is a propane or propene comprising at least one fluorine atom, in particular comprising two, three, four or five fluorine atoms, more particularly three or five fluorine atoms.

"Compound A" is understood to mean an organic compound comprising one or more carbon atoms, preferably 3 carbon atoms. The compound A is preferably a propane or a propene having one or more substituents chosen from F, Cl, I and Br (preferably from F and Cl). Preferably, the compound A is a propane or propene comprising at least one chlorine atom, two, three, four or five chlorine atoms. Preferably, the compound A has a lower degree of fluorination than that of the compound B.

It is understood that "compound B" or "compound A" is also understood to mean mixtures of compounds.

The compound B can be chosen from chlorotrifluoropropenes, pentafluoropropanes, dichlorotrifluoropropanes, trichlorodifluoropropanes, tetrachlorofluoropropanes, dichlorodifluoropropenes, trichlorofluoropropenes and a mixture of these.

The compound A can be chosen from tetrachloropropenes, chlorotrifluoropropenes, pentachloropropanes, dichlorotrifluoropropanes, trichlorodifluoropropanes, tetrachlorofluoropropanes, dichlorodifluoropropenes, trichlorofluoropropenes and the mixtures of these.

Preferably, the compound B can be chosen from the group consisting of 2-chloro-3,3,3-trifluoro-1-propene (HCFO-1233xf), 2,3-dichloro-1,1,1-trifluoropropane (HCFC-243db), 1,1,1,2,2-pentafluoropropane (HFC-245cb) and 1-chloro-3,3,3-trifluoropropene (HCFO-1233zd).

Preferably, the compound A can be chosen from the group consisting of 2-chloro-3,3,3-trifluoro-1-propene (HCFO-1233xf), 1,1,1,2,3-pentachloropropane (HCC-240db), 1,1,2,2,3-pentachloropropane (HCC-240aa), 2,3-dichloro-1,1,1-trifluoropropane (HCFC-243db), 1,1,2,3-tetrachloro-1-propene (HCO-1230xa), 2,3,3,3-tetrachloro-1-propene (HCO-1230xf), 1,1,1,3,3-pentachloropropane (HCC-240fa), 1,1,3,3-tetrachloropropene (HCO-1230za), 1,3,3,3-tetrachloropropene (HCO-1230zd), 1-chloro-3,3,3-trifluoropropene (HCFO-1233zd), 1,1,1,3-tetrachloropropane (HCC-250fb), 1,1,3-trichloropropene (HCO-1240za) and 3,3,3-trichloropropene (HCO-1240zf). Advantageously, the compound A can be different from the compound B.

In particular, the compound B can be selected from the group consisting of 2-chloro-3,3,3-trifluoro-1-propene (HCFO-1233xf) and 1,1,1,2,2-pentafluoropropane (HFC-245cb).

In particular, the compound A can be selected from the group consisting of 2-chloro-3,3,3-trifluoro-1-propene (HCFO-1233xf), 2,3-dichloro-1,1,1-trifluoropropane (HCFC-243db), 1,1,1,2,3-pentachloropropane (HCC-240db), 1,1,2,2,3-pentachloropropane (HCC-240aa), 1,1,1,3,3-pentachloropropane (HCC-240fa), 1,1,2,3-tetrachloro-1-propene (HCO-1230xa), 2,3,3,3-tetrachloro-1-propene (HCO-1230xf), 1,1,3,3-tetrachloro-1-propene (HCO-1230za) and 1,3,3,3-tetrachloro-1-propene (HCO-1230zd).

In one embodiment, the compound B is 2-chloro-3,3,3-trifluoropropene (HCFO-1233xf), in order to produce 2,3,3,3-tetrafluoropropene (HFO-1234yf).

In another embodiment, the compound B is 1-chloro-3,3,3-trifluoropropene (HCFO-1233zd), in order to produce 1,3,3,3-tetrafluoropropene (HFO-1234ze).

In another embodiment, the compound A is 1,1,1,2,3-pentachloropropane (HCC-240db) or 1,1,2,2,3-pentachloropropane (HCC-240aa) or else a mixture of the two, in order to produce 2,3,3,3-tetrafluoropropene (HFO-1234yf). In particular, the compound A is 1,1,1,2,3-pentachloropropane (HCC-240db) or 1,1,2,2,3-pentachloropropane (HCC-240aa) or else a mixture of the two; and the compound B is 2-chloro-3,3,3-trifluoropropene (HCFO-1233xf), in order to produce 2,3,3,3-tetrafluoropropene (HFO-1234yf).

According to yet another embodiment, the compound A is 2,3-dichloro-1,1,1-trifluoropropane (HCFC-243db), in order to produce 2,3,3,3-tetrafluoropropene (HFO-1234yf). In particular, the compound A is 2,3-dichloro-1,1,1-trifluoropropane (HCFC-243db) and the compound B is 2-chloro-3,3,3-trifluoropropene (HCFO-1233xf), in order to produce 2,3,3,3-tetrafluoropropene (HFO-1234yf).

According to yet another embodiment, the compound A is 1,1,2,3-tetrachloropropene (HCO-1230xa) or 2,3,3,3-tetrachloropropene (HCO-1230xf) or a mixture of these two compounds, in order to produce 2,3,3,3-tetrafluoropropene (HFO-1234yf). In particular, the compound A is 1,1,2,3-tetrachloropropene (HCO-1230xa) or 2,3,3,3-tetrachloropropene (HCO-1230xf) or a mixture of these two compounds; and the compound B is 2-chloro-3,3,3-trifluoropropene (HCFO-1233xf), in order to produce 2,3,3,3-tetrafluoropropene (HFO-1234yf).

According to yet another embodiment, the compound A is 1,1,2,3-tetrachloropropene (HCO-1230xa) or 2,3,3,3-tetrachloropropene (HCO-1230xf) or 1,1,1,2,3-pentachloropropane (HCC-240db) or a mixture of two of these or a mixture of the three; and the compound B is 2-chloro-3,3,3-trifluoropropene (HCFO-1233xf), in order to produce 2,3,3,3-tetrafluoropropene (HFO-1234yf).

According to one embodiment, the compound B is 1,1,1,2,2-pentafluoropropane (HFC-245cb), in order to produce 2,3,3,3-tetrafluoropropene (HFO-1234yf). Preferably, the compound A is 2-chloro-3,3,3-trifluoropropene (HCFO-1233xf) and the compound B is 1,1,1,2,2-pentafluoropropane (HFC-245cb), in order to produce 2,3,3,3-tetrafluoropropene (HFO-1234yf).

According to another embodiment, the compound A is 1,1,3,3-tetrachloropropene (HCO-1230za) or 1,3,3,3-tetrachloro-1-propene (HCO-1230zd) or a mixture of the two; and the compound B is 1-chloro-3,3,3-trifluoropropene (HCFO-1233zd), in order to produce 1,3,3,3-tetrafluoropropene (HFO-1234ze).

According to another embodiment, the compound A is 1,1,1,3,3-pentachloropropane (HCC-240fa) and the compound B is 1-chloro-3,3,3-trifluoropropene (HCFO-1233zd), in order to produce 1,3,3,3-tetrafluoropropene (HFO-1234ze).

According to a preferred embodiment, the regeneration stream is in the same direction or in the reverse direction, preferably in the reverse direction, with respect to the direction of introduction of a reaction stream comprising the compound B and hydrofluoric acid or the compound A and hydrofluoric acid feeding a reactor carrying out a stage of reaction of a compound B in the presence of hydrofluoric acid or a stage of reaction of a compound A in the presence of hydrofluoric acid. In particular, the direction of the regeneration stream is alternated at each regeneration stage.

According to a second aspect of the present invention, a plant 1 for the manufacture of tetrafluoropropene. Preferably, the plant 1 is configured in order to carry out the process according to the present invention described in detail above.

The plant comprises three reactors 2a, 2b, 2c for reaction in the gas phase each comprising a catalytic bed containing a catalyst or a preliminary catalyst 21a, 21b, 21c.

According to a preferred embodiment, the three reactors 2a, 2b, 2c for reaction in the gas phase are each configured in order to be fed by:
    a device for feeding with reaction stream 16 comprising a compound B and hydrofluoric acid; and/or
    a device for feeding with preliminary reaction stream 20 comprising a compound A and hydrofluoric acid; and/or
    a device for feeding with regeneration stream 11 configured in order to feed the reactor with a regeneration stream comprising an oxidizing agent;
    optionally, a device for feeding with waiting stream 14 configured in order to feed the reactor with an inert gaseous stream comprising an inert gas.

Preferably, the amount of catalyst or of preliminary catalyst n in the catalytic bed 21a, 21b, 21c of one of the reactors 2a, 2b, 2c is from 90% to 110% of the amount of catalyst or of preliminary catalyst present in the catalytic bed of one of the other two reactors.

According to a specific embodiment, the amount of catalyst or of preliminary catalyst present in the catalytic bed of each reactor is between 90% and 110% of the amount of catalyst or of preliminary catalyst present in the catalytic bed of the other two reactors considered independently of one another, advantageously between 92% and 108%, preferably between 95% and 105%, in particular between 98% and 102%.

Preferably, as explained above with reference to the process, the amount of catalyst or of preliminary catalyst present in the catalytic bed 21a, 21b, 21c of each reactor 2a, 2b, 2c is identical in the three reactors.

According to a preferred embodiment, the plant is configured so that, when the first reactor 2a is fed by the device for feeding with reaction stream 16, the second reactor 2b is fed by the device for feeding with regeneration stream 11. Preferably, the device for feeding with regeneration stream 11 is connected at the top and at the bottom of the reactor. In particular, the plant is configured so that the device for feeding with regeneration stream 11 feeds any one of the three reactors at the bottom and at the top alternately.

According to a preferred embodiment, the tetrafluoropropene is 2,3,3,3-tetrafluoropropene or 1,3,3,3-tetrafluoropropene. The compounds A and B are as described above in connection with the process for the manufacture of tetrafluoropropene.

The plant can comprise:
    a first reactor 2a, a second reactor 2b and a third reactor 2c;
    a first device for collecting stream of products resulting from the first reactor 18a connected at the outlet of the latter;

a second device for collecting stream of products resulting from the second reactor 18b connected at the outlet of the latter;

a third device for collecting stream of products resulting from the third reactor 18c connected at the outlet of the latter;

a first intermediate collecting device 13 connected to any one of the devices for collecting stream of products 18a, 18b, 18c and joined to the device for feeding with preliminary reaction stream 20;

a second intermediate collecting device 19 connected to any one of the devices for collecting stream of products 18a, 18b, 18c and joined to the separation unit 4;

a separation unit 4 fed by the second intermediate collecting device 19;

a first collecting pipe 15 and a second collecting pipe 17 which are connected at the outlet of the separation unit 4, the first collecting pipe 15 being configured in order to transport a stream comprising hydrochloric acid and tetrafluoropropene and the second collecting pipe 17 being configured in order to transport a stream comprising hydrofluoric acid and compound B;

a device for feeding with reaction stream 16 configured in order to feed the first reactor 2a, the second reactor 2b and the third reactor 2c, this device being itself fed by a device for feeding with hydrofluoric acid 10 and optionally by the second collecting pipe 17;

a device for feeding with preliminary reaction stream 20 configured in order to feed the first reactor 2a, the second reactor 2b and the third reactor 2c, this device being itself fed by a device for feeding with hydrofluoric acid 10 and optionally by the first intermediate collecting device 13;

a device for feeding with regeneration stream 11 configured in order to feed the first reactor 2a, the second reactor 2b and the third reactor 2c;

a device for collecting stream of gas resulting from the regeneration 12 of the first reactor 2a, of the second reactor 2b and of the third reactor 2c.

Alternatively, the plant can comprise:

a first reactor 2a, a second reactor 2b and a third reactor 2c;

a first device for collecting stream of products resulting from the first reactor 18a connected at the outlet of the latter;

a second device for collecting stream of products resulting from the second reactor 18b connected at the outlet of the latter;

a third device for collecting stream of products resulting from the third reactor 18c connected at the outlet of the latter;

a third intermediate collecting device 3 connected to any one of the devices for collecting stream of products 18a, 18b, 18c and joined to the device for feeding with reaction stream 16;

a second intermediate collecting device 19 connected to any one of the devices for collecting stream of products 18a, 18b, 18c and joined to the separation unit 4;

a separation unit 4 fed by the second intermediate collecting device 19;

a first collecting pipe 15 and a second collecting pipe 17 which are connected at the outlet of the separation unit 4, the first collecting pipe 15 being configured in order to transport a stream comprising hydrochloric acid and tetrafluoropropene and the second collecting pipe 17 being configured in order to transport a stream comprising hydrofluoric acid and compound B;

a device for feeding with reaction stream 16 configured in order to feed the first reactor 2a, the second reactor 2b and the third reactor 2c, this device being itself fed by a device for feeding with hydrofluoric acid 10, and by the third intermediate collecting device 3 and optionally by the second collecting pipe 17;

a device for feeding with preliminary reaction stream 20 configured in order to feed the first reactor 2a, the second reactor 2b and the third reactor 2c, this device being itself fed by a device for feeding with hydrofluoric acid 10 and optionally by the second collecting pipe 17;

a device for feeding with regeneration stream 11 configured in order to feed the first reactor 2a, the second reactor 2b and the third reactor 2c;

a device for collecting stream of gas resulting from the regeneration 12 of the first reactor 2a, of the second reactor 2b and of the third reactor 2c.

Preferably, the reaction stream comprises said compound B and optionally hydrofluoric acid. The preliminary reaction stream can comprise said compound A and optionally hydrofluoric acid.

The plant can also comprise a device for feeding with waiting stream 14 configured in order to feed the first reactor 2a, the second reactor 2b and the third reactor 2c with an inert gaseous stream. Thus, the plant also comprises a device for collecting an inert gas stream 23 resulting from the first reactor 2a, from the second reactor 2b and from the third reactor 2c.

Figure 3A:
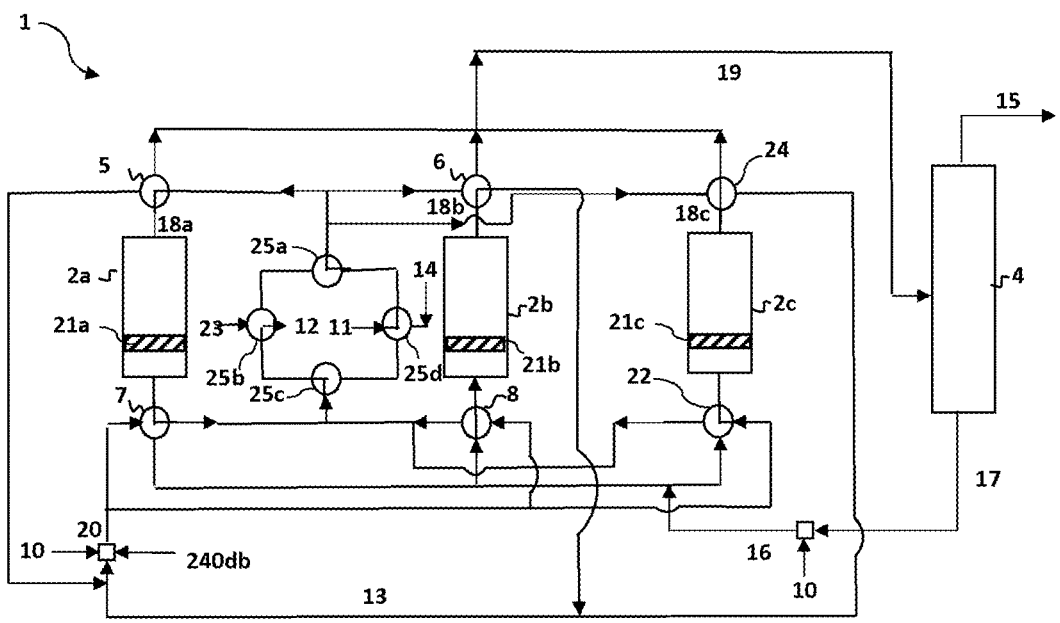
FIGS. 3a and 3b diagrammatically represent an embodiment of a plant according to the invention with three reactors comprising a device for feeding with regeneration stream at the reactor bottom and at the reactor top, in two different configurations.

The device for feeding with waiting stream 14 and the device for feeding with regeneration stream 11 can be configured in order to feed, at the top and at the bottom, any one of the three reactors 2a, 2b, 2c. This can be carried out by a suitable device, for example a set of valves 25a, 25b, 25c, 25d as represented in FIG. 3a and in FIG. 3b.

The reactors 2a, 2b, 2c are preferably made of steel and have an interior surface covered with an alloy comprising more than 30% by weight of nickel or with a coating of fluoropolymers type; preferably, the alloy comprising more than 30% by weight of nickel is an Incolloy®, Inconel®, Monel® or Hastelloy®.

The plant will be described below in a detailed way in connection with FIGS. 1a to 4, without being limited thereto. In the description below, the compound A is, for example, 1,1,1,2,3-pentachloropropane (HCC-240db).

FIG. 1a illustrates a plant according to an embodiment of the present invention in which a stage of reaction of a compound A HCC-240db is carried out in the first reactor 2a. A stream 10 comprising hydrofluoric acid also feeds the reactor 2a in order to make possible the reaction between the HCC-240db and HF via the device for feeding with preliminary reaction stream 20. The valve 7 is configured for this purpose. The first reactor 2a comprises the catalytic bed 21a. The first device for collecting stream of products 18a resulting from the first reactor 2a and connected at the outlet of the latter feeds the second intermediate collecting device 19, itself connected to the separation unit 4. The first device for collecting stream of products 18a and the second intermediate collecting device 19 comprise in particular a stream of products comprising at least HCFO-1233xf, HF and HCl, and optionally HFO-1234yf and HFC-245cb. The latter stream is separated, at the separation unit 4, into a first stream comprising HCl and optionally HFO-1234yf in the first collecting pipe 15 and, in the second collecting pipe 17, into a second stream comprising HCFO-1233xf, HF and possibly HFC-245cb. The second collecting pipe 17 is connected to the device for feeding with reaction stream 16, itself fed with hydrofluoric acid 10. The device for feeding with reaction stream 16 feeds the third reactor 2c comprising a catalytic bed 21c. In this third reactor, the compound B, in this instance HCFO-1233xf, is subjected to a catalytic reaction in order to form a stream of products comprising HFO-1234yf and HFC-245cb which is collected at the outlet of the reactor by the third device for collecting stream of products 18c. The third device for collecting stream of products 18c resulting from the third reactor feeds the first intermediate collecting device 13 joined to the device for feeding with preliminary reaction stream 20. The second reactor 2b comprising the catalytic bed 21b is in the regeneration phase. The reactor 2b is thus fed with a regeneration stream conveyed by the device for feeding with regeneration stream 11 via the valve 8 configured for this purpose. The second device for collecting the stream of the products 18b resulting from the second reactor is connected to the device for collecting stream of gas resulting from the regeneration 12 via a valve 6 configured for this purpose. The process is carried out continuously.

Figure 1B:
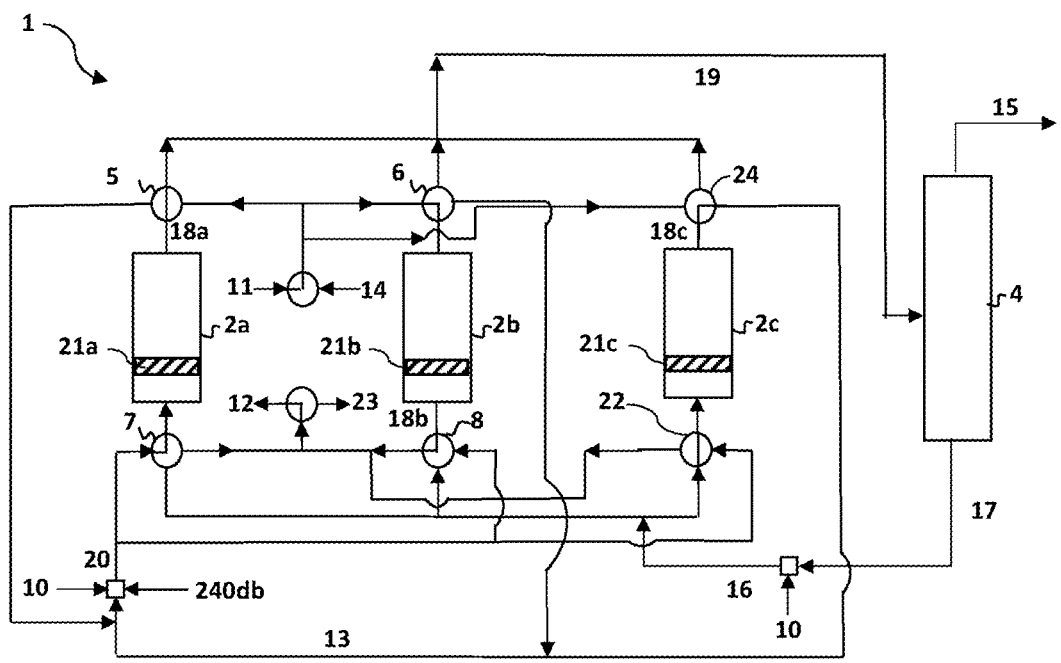

FIG. 1b illustrates a plant according to an embodiment of the present invention in which the direction of the regeneration stream is modified with respect to that of the embodiment illustrated in FIG. 1a. To this end, the regeneration stream feeds the second reactor 2b by the top of the reactor. The direction of the regeneration stream is thus reversed with respect to the direction of introduction of the reaction stream and of the preliminary reaction stream in, respectively, the first reactor 2a and the third reactor 2c.

Figure 2A:
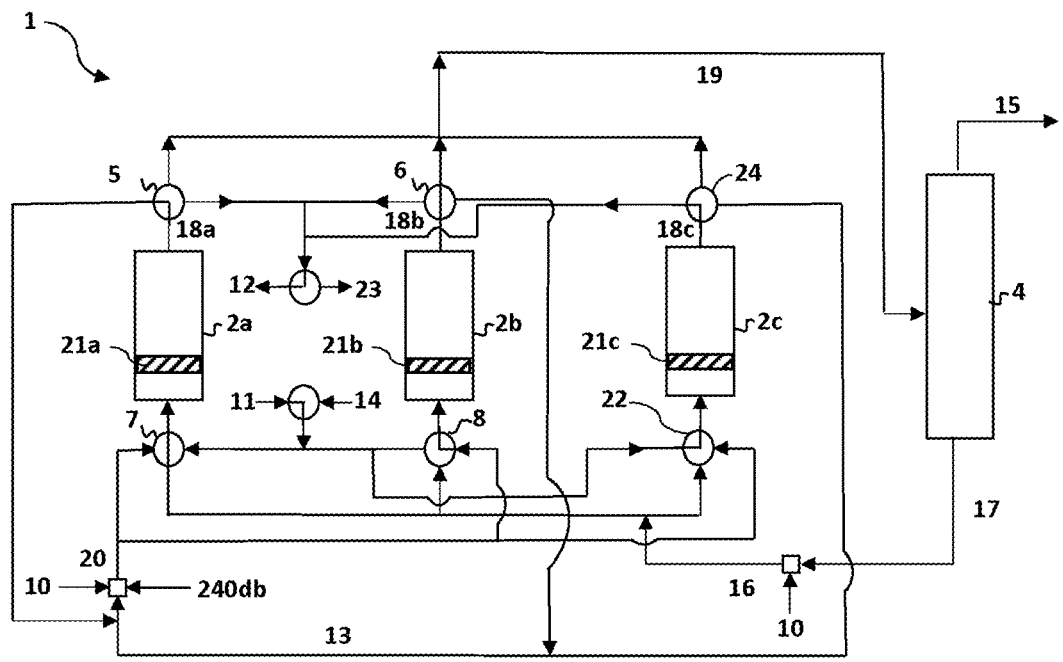
FIGS. 2a, 2b and 2c diagrammatically represent an embodiment of a plant according to the invention with three reactors in different operating configurations.

FIG. 2a illustrates a plant according to an embodiment of the present invention in which a reaction between the compound B, HCFO-1233xf and HF is carried out in the first reactor 2a, a reaction between HCC-240db and HF is carried out in the second reactor 2b and a regeneration of the catalyst is carried out in the third reactor 2c. The device for feeding with preliminary stream 20 is fed with hydrofluoric acid 10 and HCC-240db and by the first intermediate collecting device 13. The device for feeding with preliminary stream 20 is connected to the second reactor 2b; the valve 8 is configured for this purpose. The second device for collecting the stream of products 18b resulting from the second reactor 2b is joined to the second intermediate collecting device 19, the latter being connected to the separation unit 4. The second collecting pipe 17 feeds the device for feeding with reaction stream 16 feeding the first reactor 2a. The first device for collecting the stream of products 18a resulting from the first reactor 2a is configured in order to feed the first intermediate collecting device 13 via the valve 5. The third reactor 2c is in the regeneration phase. The latter is thus fed with regeneration stream by the device for feeding with regeneration stream 11 via the valve 22 configured for this purpose. The third device for collecting stream of products 18c from the third reactor is connected to the device for collecting the stream of gas resulting from the regeneration 12 via the valve 24.

Figure 2B:
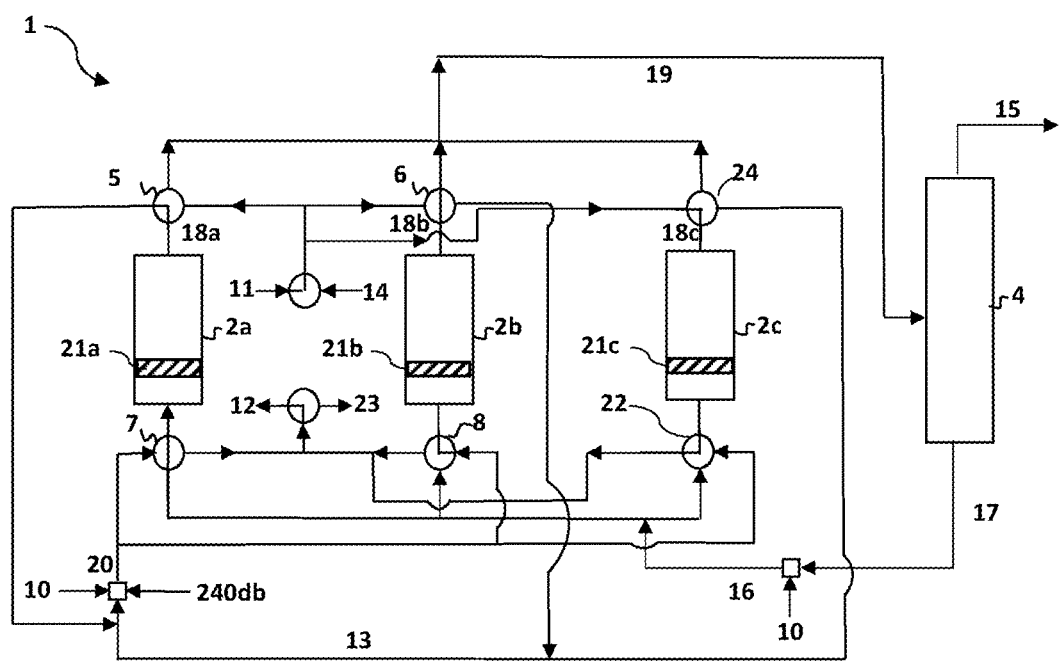

With respect to FIG. 2a, FIG. 2b illustrates a plant according to an embodiment of the present invention in which the regeneration stream feeds the third reactor 2c by the top of the latter. The direction of the regeneration stream is thus reversed with respect to the stream of the reaction mixture or of the preliminary mixture which respectively feed the second reactor 2b and the first reactor 2a by the bottom of the reactor.

Figure 2C:
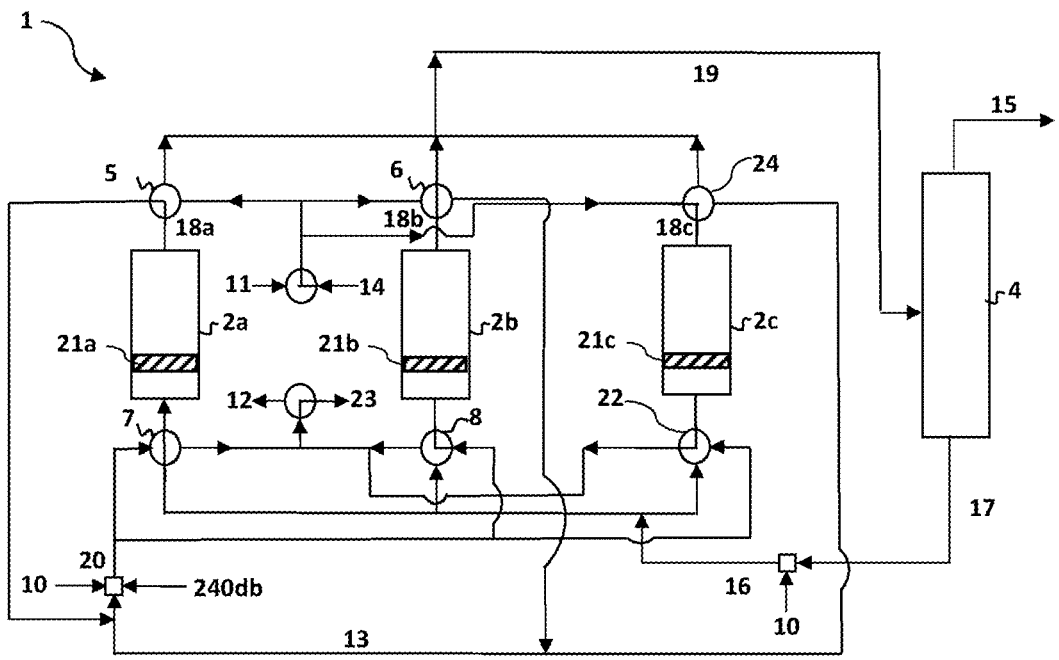

With respect to FIG. 2b, FIG. 2c illustrates a plant according to an embodiment of the present invention in which the third reactor is fed with an inert gas stream instead of a regeneration stream. The third reactor 2c is thus connected to the device for feeding with waiting stream 14 comprising an inert gas. The device for collecting stream of products 18c from the third reactor is connected to the device for collecting the inert gas stream 23.

With respect to FIG. 1a, FIG. 3a illustrates a plant according to an embodiment of the present invention in which the reactors can be fed with a regeneration stream at the top and at the bottom of the reactor alternately. The valves 25a, 25b, 25c and 25d are configured in order to make it possible to feed the third reactor 2c either by the top or the bottom of the latter with a regeneration stream resulting from the device for feeding with regeneration stream 11 according to the same principle as that described in detail for FIG. 1a. The same principle can be applied with the stream resulting from the device for feeding with inert gas 14.

Figure 3B:
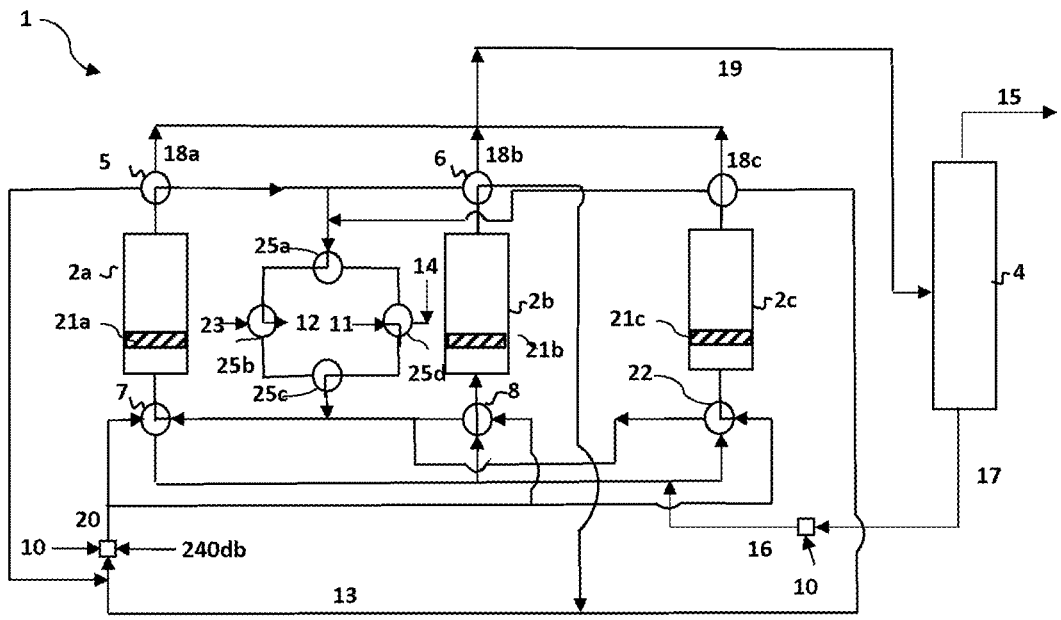

With respect to FIG. 3a, FIG. 3b illustrates a plant according to an embodiment of the present invention in which the first reactor 2a is in the regeneration phase instead of the third reactor 2c.

Figure 4:
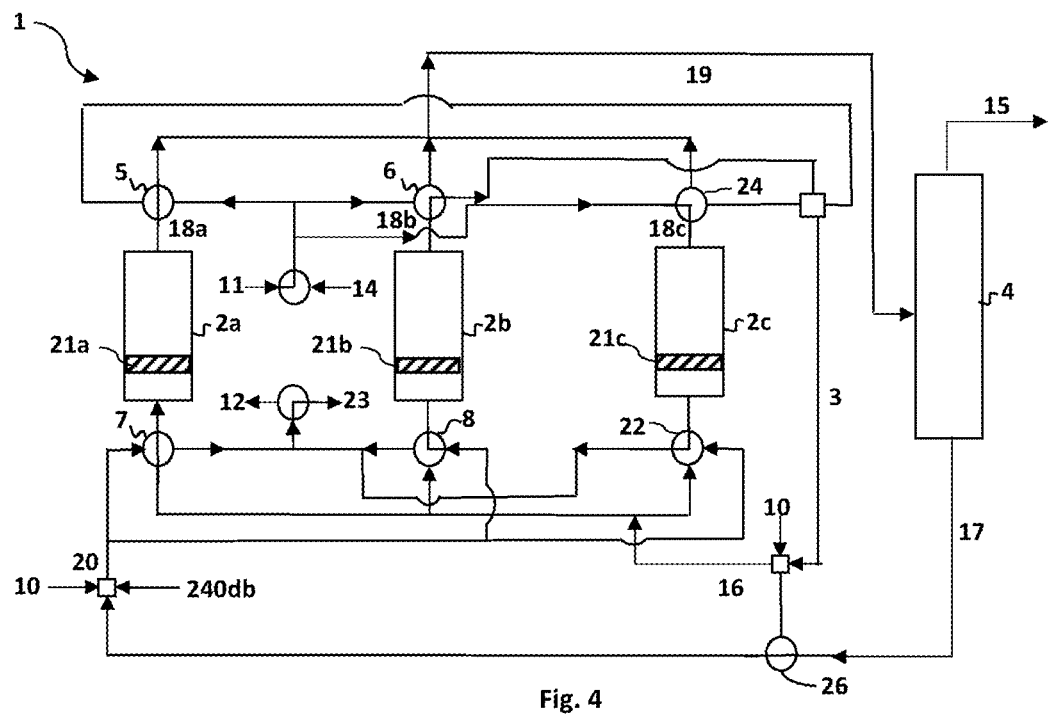
FIG. 4 diagrammatically represents an embodiment of a plant according to the invention in which the separation unit is in a different operating configuration.

FIG. 4 illustrates a plant according to another embodiment of the present invention. The plant 1 comprises a third intermediate collecting device 3 feeding the device for feeding with reaction mixture 16 instead of the first intermediate collecting device 13. The third reactor 2c is in the regeneration phase, as explained above in FIG. 2b. The second reactor 2b is fed by the device for feeding with preliminary reaction stream 20. The second device for collecting stream of products 18b at the outlet of the second reactor 2b is connected to the third intermediate collecting device 3. The latter feeds the device for feeding with reaction stream 16. The first reactor 2a is fed by the device for feeding with reaction stream 16. The first device for collecting stream of products 18a at the outlet of the first reactor 2a is joined to the second intermediate collecting device 19. The stream of products resulting from the first reactor 2a comprises HCFO-1233xf, HCC-240db, HFO-1234yf, HF and HCl. This stream is separated in the separation unit 4, as explained above. The second collecting pipe 17 can feed either the device for feeding with reaction stream 16 or the device for feeding with preliminary reaction stream 20 via the valve 26, which can be configured for either alternative.

The invention makes it possible to optimize the manufacture of tetrafluoropropene (HFO-1234yf or HFO-1234ze) by alternating the cycles of regeneration and of manufacture of the tetrafluoropropene with three reactors comprising the same amount of catalyst. The invention also makes it possible to improve the regeneration stage by making it possible to carry out the latter alternately by the bottom or the top of the reactor in order to prevent the accumulation of coke in the reactor.

The invention claimed is:

1. A process for the manufacture of tetrafluoropropene employing three reactors, each comprising a catalytic bed containing a catalyst or a preliminary catalyst and comprising the implementation, independently in each of the reactors:

reacting a compound A in the gas phase in the presence of hydrofluoric acid and a preliminary catalyst, to form a compound B;

reacting a compound B in the gas phase in the presence of hydrofluoric acid and a catalyst, to form the tetrafluoropropene, or regenerating the catalyst or the preliminary catalyst by bringing the latter into contact with a regeneration stream comprising an oxidizing agent, wherein the amount of catalyst or of preliminary catalyst in the catalytic bed of one of the reactors represents between 90% and 110% of the amount of catalyst or of preliminary catalyst present in the catalytic bed of one of the other two reactors, and
wherein reacting compound B is carried out in one of the three reactors while reacting compound A is carried out in one of the other two reactors.

2. The process as claimed in claim 1, wherein the amount of catalyst or of preliminary catalyst present in the catalytic bed of each reactor is between 90% and 110% of the amount of catalyst or of preliminary catalyst present in the catalytic bed of the other two reactors considered independently of one another.

3. The process as claimed in claim 1, wherein the amount of catalyst or of preliminary catalyst present in the catalytic bed of each reactor is identical in the three reactors.

4. The process as claimed in claim 1, wherein the reacting of compound B in the presence of hydrofluoric acid or the reacting of compound A in the presence of hydrofluoric acid is carried out alternately with regenerating the catalyst or the preliminary catalyst.

5. The process as claimed in claim 1, wherein the process simultaneously employs:
   reacting compound B in the presence of hydrofluoric acid in one of the three reactors;
   reacting compound A in the presence of hydrofluoric acid in another of the three reactors;
   regenerating the catalyst or the preliminary catalyst or a waiting stage in the third reactor.

6. The process as claimed in claim 1, wherein the process comprises:
   collecting a stream of products on conclusion of the reacting of the compound B;
   using said stream of products collected on conclusion of the reacting of the compound B in order to carry out the reacting of the compound A in the presence of hydrofluoric acid; and
   separating the stream of products resulting from the reacting of the compound A in the presence of hydrofluoric acid into a first stream comprising hydrochloric acid and tetrafluoropropene and a second stream comprising hydrofluoric acid and the compound B;
   optionally, collecting said second stream comprising hydrofluoric acid and the compound B, and recycling the second stream in the reacting of the compound B in the presence of hydrofluoric acid or of the reacting of the compound A.

7. The process as claimed in claim 1, wherein the compound A is selected from the group consisting of tetrachloropropenes, chlorotrifluoropropenes, pentachloropropanes, dichlorotrifluoropropanes, trichlorodifluoropropanes, tetrachlorofluoropropanes, dichlorodifluoropropenes, trichlorofluoropropenes and the mixtures of these; and the compound B is selected from the group consisting of chlorotrifluoropropenes, pentafluoropropanes, dichlorotrifluoropropanes, trichlorodifluoropropanes, tetrachlorofluoropropanes, dichlorodifluoropropenes, trichlorofluoropropenes and the mixtures of these.

8. The process as claimed in claim 1, wherein the tetrafluoropropene comprises 2,3,3,3-tetrafluoropropene or 1,3,3,3-tetrafluoropropene.

9. A process for the manufacture of tetrafluoropropene employing three reactors, each comprising a catalytic bed containing a catalyst or a preliminary catalyst and comprising the implementation, independently in each of the reactors:
   reacting a compound A in the gas phase in the presence of hydrofluoric acid and a preliminary catalyst, to form a compound B;
   reacting a compound B in the gas phase in the presence of hydrofluoric acid and a catalyst, to form the tetrafluoropropene, or
   regenerating the catalyst or the preliminary catalyst by bringing the latter into contact with a regeneration stream comprising an oxidizing agent,
wherein the amount of catalyst or of preliminary catalyst in the catalytic bed of one of the reactors represents between 90% and 110% of the amount of catalyst or of preliminary catalyst present in the catalytic bed of one of the other two reactors, and
wherein a regeneration stage is carried out in one of the three reactors while reacting compound B is carried out in one of the other two reactors.

10. The process of claim 9, wherein while a regeneration stage is carried out in one of the three reactors and reacting compound B is carried out in one of the other two reactors, reacting compound A is carried out in the third reactor.

* * * * *